United States Patent [19]

Ray

[11] Patent Number: 5,281,223
[45] Date of Patent: Jan. 25, 1994

[54] TOOL AND METHOD FOR DEROTATING SCOLIOTIC SPINE

[76] Inventor: R. Charles Ray, 5425-87th Ave. West, Tacoma, Wash. 98467

[21] Appl. No.: 949,103

[22] Filed: Sep. 21, 1992

[51] Int. Cl.$^5$ .......................... A61B 17/56; A61F 5/00
[52] U.S. Cl. ...:...................................... 606/61; 606/86
[58] Field of Search ...................... 606/62, 86, 87, 88, 606/83; 81/315, 318, 320, 324, 325, 326, 327, 334, 335, 415, 418, 424.5, 426.5, 427.5

[56] References Cited

U.S. PATENT DOCUMENTS

| | | | |
|---|---|---|---|
| 717,526 | 1/1903 | Barney | 81/424.5 |
| 1,119,532 | 12/1914 | Parks | 81/424.5 |
| 2,583,896 | 1/1952 | Siebrandt | 606/86 |
| 3,181,340 | 5/1965 | Gruetzmacher | 81/426.5 |
| 4,361,141 | 11/1982 | Tanner | 128/69 |
| 4,382,438 | 5/1983 | Jacobs | 128/69 |
| 4,386,461 | 6/1983 | Plummer | 81/424.5 |
| 4,601,221 | 7/1986 | Kalkbrenner | 81/418 |
| 4,697,483 | 10/1987 | Rodgers | 81/424 |
| 4,863,476 | 9/1989 | Shepperd | 623/17 |
| 5,010,879 | 4/1991 | Moriya | 606/61 |
| 5,122,130 | 6/1992 | Keller | 606/61 |

FOREIGN PATENT DOCUMENTS

| | | |
|---|---|---|
| 1074514 | 2/1984 | U.S.S.R. . |
| 1281264 | 1/1987 | U.S.S.R. . |
| 1581303 | 7/1990 | U.S.S.R. . |

OTHER PUBLICATIONS

Texas Scottish Rite Hospital (TSRH) Universal Spinal Instrumentation System, by Charles E. Johnston, II, J. Anthony Herring, and Richard B. Ashman, pp. 127-165.
Cotrel-Dubousset Instrumentation, by Richard A. Balderston, pp. 113-126.
Cotrel-Dubousset Instrumentation in the Treatment of Idiopathic Scoliosis, by Francis Dennis, M.D., Orthopedic Clinics of North America, vol. 19, No. 2, Apr. 1988, pp. 291-311.
Idiopathic Scoliosis Posterior Spine Fusion With Harrington Rod and Sublaminar Wiring, by Barry J. Silverman, M.D., and Phillip E. Greenberg, M.D., Orthopedic Clinics of North America, vol. 19, No. 2, Apr. 1988, pp. 269-279.
Analysis of Pulmonary Function and Axis Rotation in Adolescent and Young Adult Idiopathic Scoliosis Patients Treated With Cotrel-Dubousset Instrumentation, by Lawrence G. Lenke, Keith H. Bridwell, et al., Journal of Spinal Disorders, vol. 5, No. 1, pp. 16-254, 1992.
Rotational Changes of the Vertebral-Pelvic Axis Following Cotrel-Dubousset Instrumentation, by Kirkham B. Wood, M.D., et al., Twin Cities Scoliosis Spine Center, Department of Orthopaedic Surgery, University of Minnesota, Minneapolis, Minn., vol. 16, No. 8 Supplement, 1991.
Derotational Analysis of Cotrel-Dubousset Instrumentation in Idiopathic Scoliosis, by John M. Gray, M.D., et al., Shriners Hospital for Crippled Children, Children's Hospital, San Francisco, Calif., and the Department of Orthopaedic Surgery, University of California, San Francisco, Calif., vol. 16, No. 8 Supplement, 1991.

Primary Examiner—Michael A. Brown
Attorney, Agent, or Firm—Christensen, O'Connor, Johnson & Kindness

[57] ABSTRACT

A tool and method for derotating a scoliotic spine while it is being manipulated from a scoliotic configuration to a kyphotic configuration. The tool is used to apply a derotating force to the convex side of the scoliotic spine. The method uses the tool to reduce the derotation of a scoliotic spine.

19 Claims, 6 Drawing Sheets

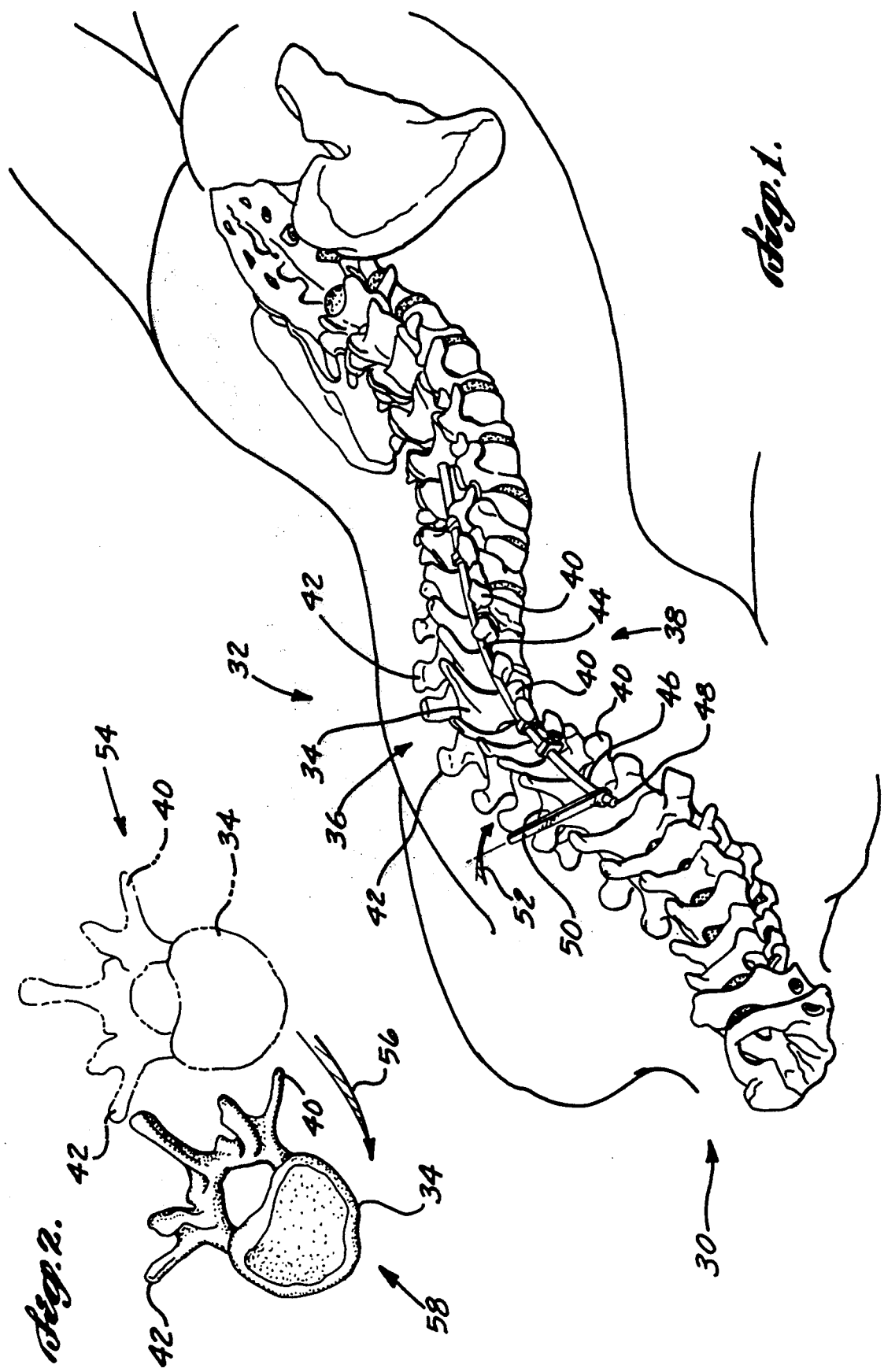

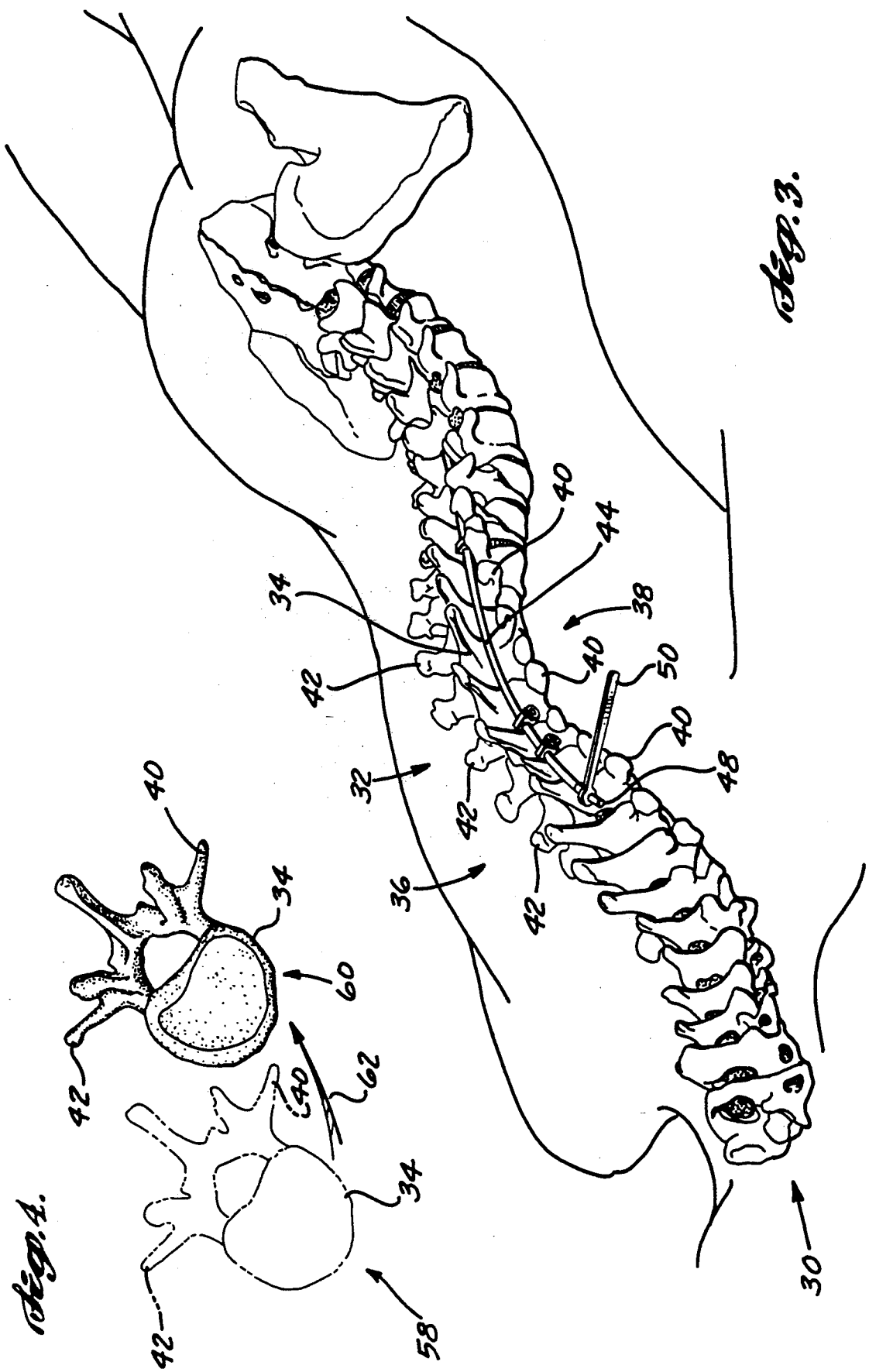

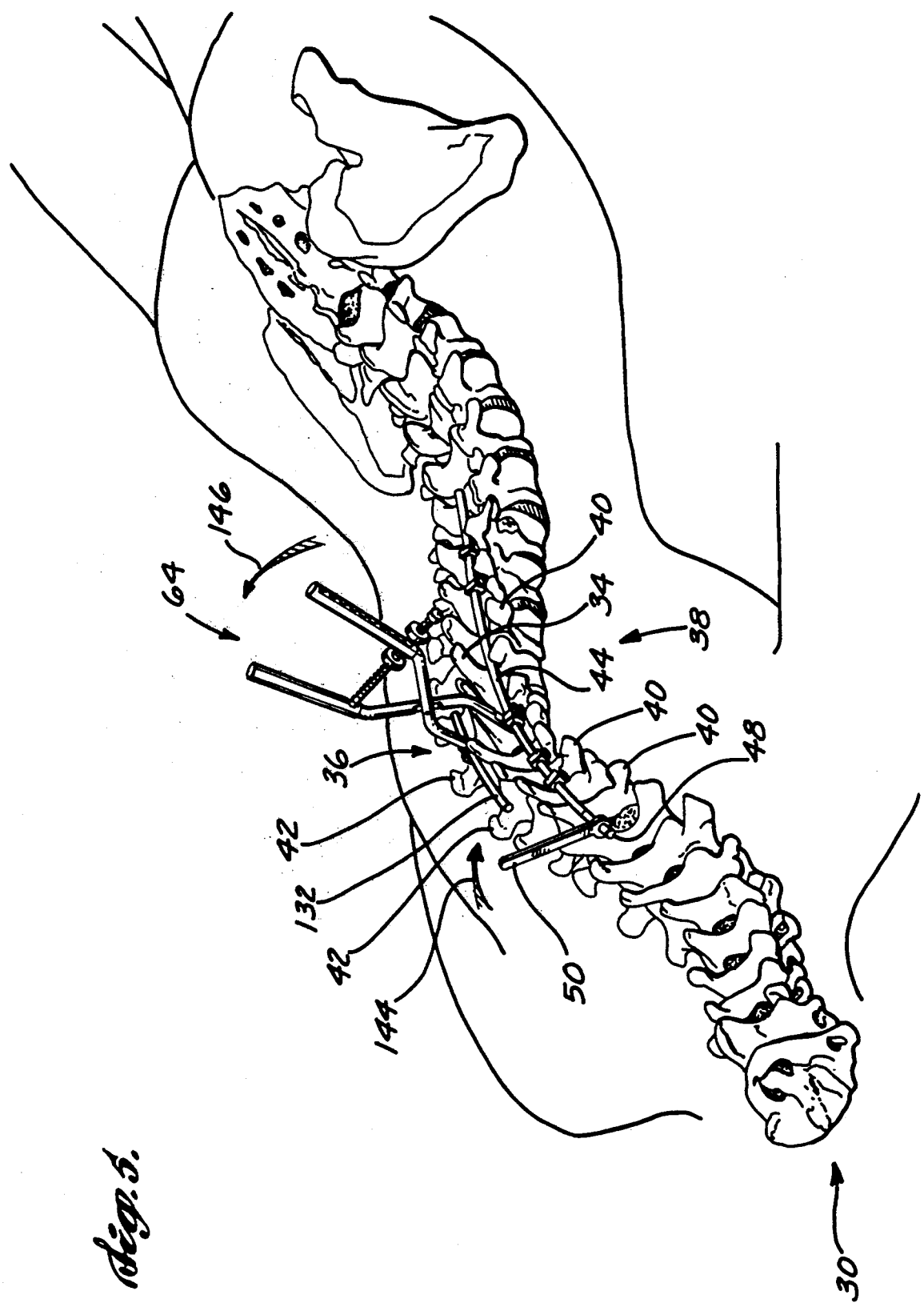

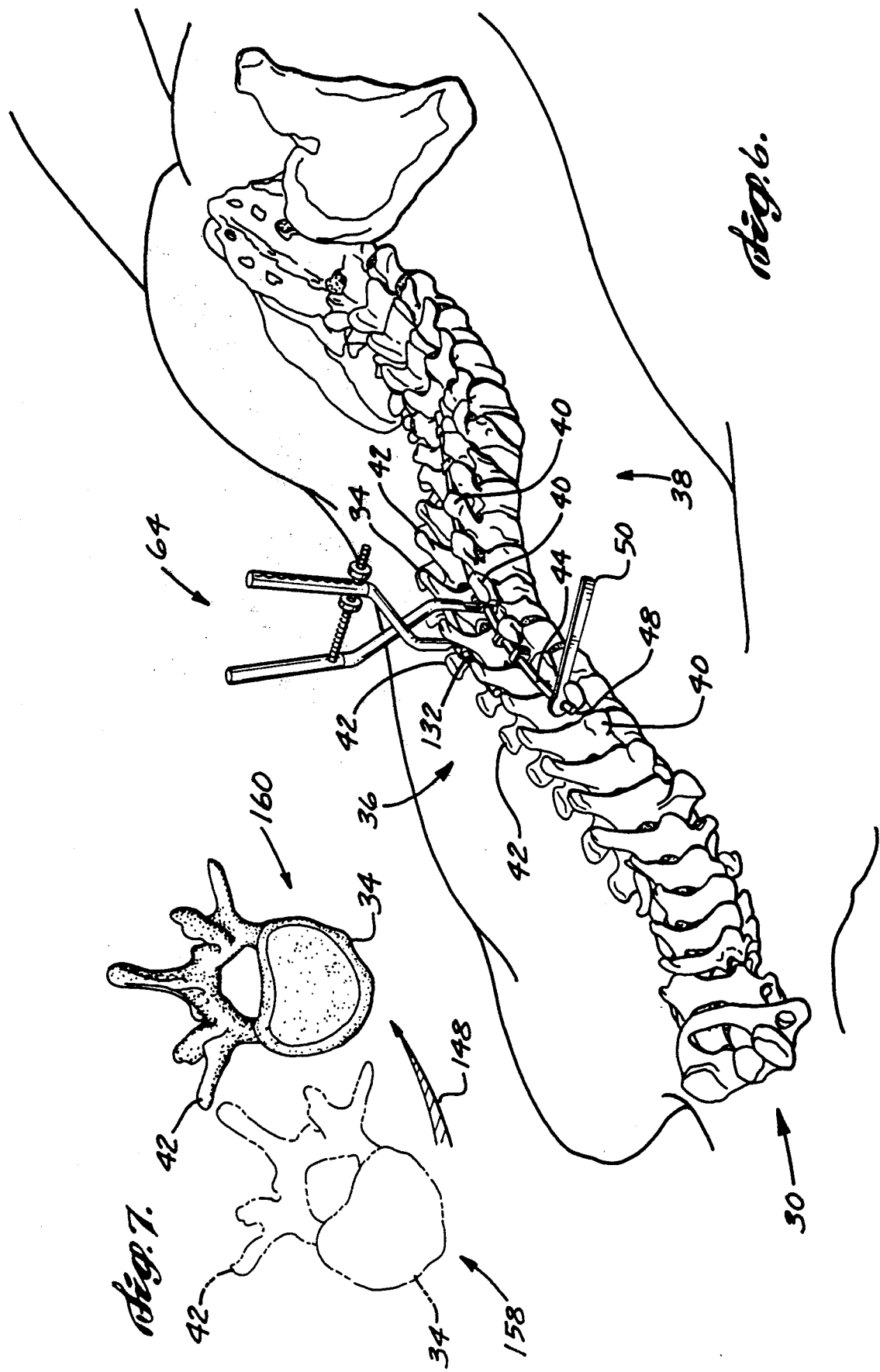

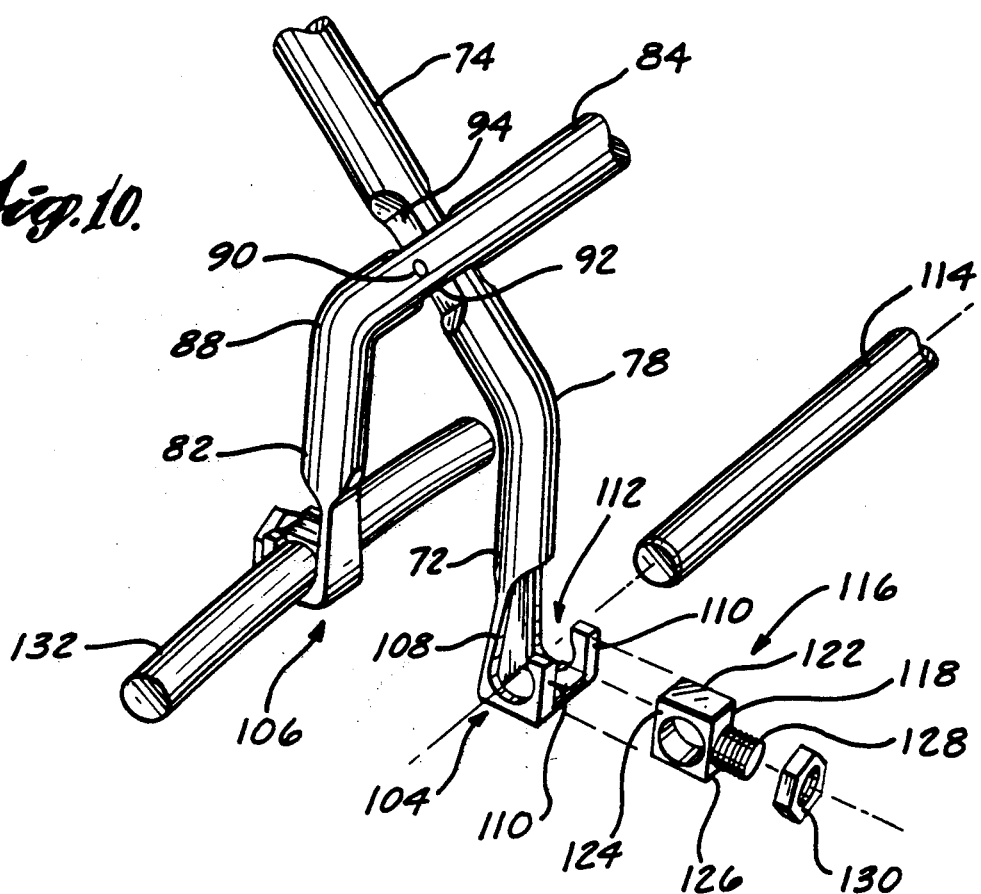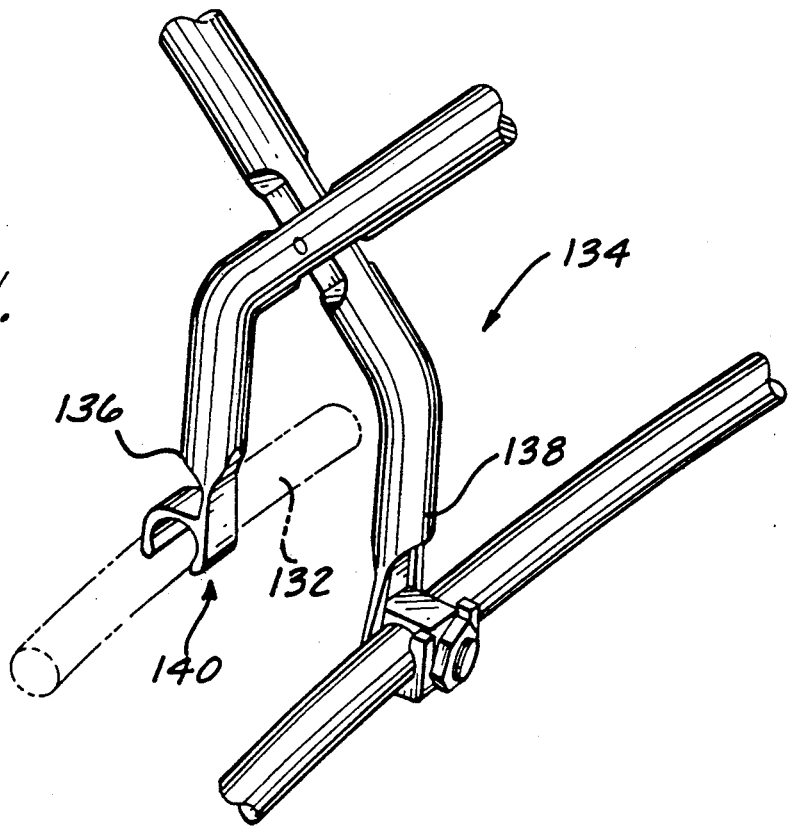

TOOL AND METHOD FOR DEROTATING SCOLIOTIC SPINE

FIELD OF THE INVENTION

The present invention relates to tools and methods for treating spinal deformities, particularly the spinal condition known as scoliosis.

BACKGROUND OF THE INVENTION

The normal spine when viewed in an anterior posterior direction is straight. The same spine, when viewed from the lateral view has a series of curvatures. The thoracic curvature has a convexity posteriorly (in the sagittal plane). The lumbar spine has a curvature with the convexity directed anteriorly. Scoliosis, traditionally, has been discussed as a side bending (in the coronal plane) of the normally straight spine when viewed from the anterior-posterior direction. Depending on the etiology, there may be just one primary curve having smaller secondary compensatory curves, or there may be several primary curves. The stiffness of the curve varies between individuals dependent upon the amount of bone deformity and ligamentous contracture that has occurred over a period of time. Harrington's first apparatus for aligning the spine was a straight rod attached at a single site top and bottom. This did an excellent job of straightening the lateral curvature (coronal plane) but ignored the normal sagittal plane curvatures of the spine. This resulted in a worsening of the spinal alignment in the sagittal plane in many cases.

Scoliosis now is fully appreciated to be a deformity of the spine in three planes. This deformity results in the appearance of (1) a lateral bend on the anterior posterior view, (2) a loss of the normal convexity posterior curvature of the thoracic area or a straightening of the spine on the lateral view and (3) a rotational deformity of the apical vertebra, wherein the transverse process of the apical vertebra on the convex side rotates posteriorly and the transverse process of the apical vertebra on the concave side rotates anteriorly.

Cotrel attempted to deal with all three aspects of this deformity by changing the instrumentation with the Cotrel-Dubousset (C-D) technique. The C-D instrumentation for the correction and stabilization of spinal deformity was introduced to the Scoliosis Research Society in 1984. The C-D instrumentation was subsequently modified by Texas Scottish Rite Hospital (TSRH) in 1985. Both the C-D and TSRH instrumentation include a curved rod designed with multiple hooks for attachment to the spine. The rod is first applied to the concave side of the curve. The instrumentation allows rotation between the hooks and the rod so that the rod is placed in the spine in a scoliotic position, that is with the curvature of the rod matching the curvature of the deformity. The rod is then rotated 90 degrees converting the scoliosis into kyphosis. This helps decrease the lateral curvature of the spine in the anterior posterior direction and also helps increase the insufficient curvature in the sagittal plane. It initially was hoped that this also would reduce the rotation of the apical vertebra. The results in this last case have been disappointing. Since this technique still relies primarily on a single rod pulling in a single direction for correction, it is understandable how this cannot effectively derotate the vertebra.

In view of the shortcomings of the existing procedures for treating scoliotic spines, there is a need for improvements which will allow practitioners to apply forces lifting the concave side while simultaneously compressing the convex side, thus imparting a derotational torque while at the same time correcting both saggital and coronal plane deformity.

SUMMARY OF THE INVENTION

The present invention is a method and apparatus for derotating a scoliotic spine at the same time that lateral curvature of the deformed spine is treated, e.g., by using the Cotrel-Dubousset technique and instrumentation. A method and tool formed in accordance with the present invention enables the practitioner to derotate the vertebrae around the apical vertebra. A method and tool formed in accordance with the present invention has the added advantage of complementing existing techniques for treating a scoliotic spine.

A method carried out in accordance with the present invention is used to treat a scoliotic spine that can be described as having a convex side and a concave side. The concave side refers to the inside of the lateral curvature and the convex side refers to the exterior of the lateral curvature. The method involves the steps of connecting a derotation rod to the scoliotic spine. The derotation rod has a scoliotic configuration and a kyphotic configuration. The derotation rod is in its scoliotic configuration when it is initially affixed to the spine. The kyphotic configuration is the position that the derotation rod occupies after the method is completed. The kyphotic configuration is designed to remove the lateral curvature as well as introduce kyphosis back into the spine. After the derotation rod is connected to the scoliotic spine, it is rotated from its scoliotic configuration to its kyphotic configuration. This rotation of the rod pulls the spine to reduce the lateral curvature, and also pulls the spine in a posterior direction. In accordance with the present invention, the rotational deformity of the scoliotic spine is reduced during this rotating step by applying a pushing force in an anterior direction to the convex side of the scoliotic spine while pulling posteriorly on the concave side. This combination of two forces acting simultaneously is needed to achieve a derotation of the apical vertebra.

In one embodiment, the force on the convex side of the scoliotic spine is created by securing a tool to the derotation rod and manually biasing the tool in the desired direction.

Such a tool includes a first arm member that includes a first handle end and a first nose end opposite the first handle end. The first handle end and the first nose end are connected by a first neck. The tool also includes a second arm member having a second handle end and a second nose end opposite the second handle end, the second handle end and the second nose end being connected by a second neck. The first arm member and the second arm member are pivotally connected at the first neck and the second neck. A first coupling member is secured to the first nose end for securing the first arm member to a derotation rod. A second coupling member is provided on the second nose end for securing the second arm member to a force imparting rod. The force imparting rod is used to apply force in an anterior direction to the convex side of the scoliotic spine.

In one embodiment of the tool, an adjustment bolt is secured to the first arm member and slidably engages the second arm member near the first and second handle ends. The adjustment bolt carries an inner adjustment nut and an outer adjustment nut. The inner and outer adjustment nuts are on opposite sides of the second arm member.

In still another embodiment of the tool formed in accordance with the present invention, the second nose end includes an integral force imparting rod attached thereto.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 1 is a perspective view from the concave and posterior sides of a scoliotic spine carrying TSRH instrumentation in its scoliotic configuration;

FIG. 2 is a plan view in the caudal direction of the apical vertebra of the scoliotic spine in FIG. 1 in its deformed configuration (solid lines) and a normal configuration (ghost lines);

FIG. 3 is a perspective view from the concave and posterior side of the scoliotic spine in FIG. 1 carrying TSRH instrumentation in the kyphotic configuration;

FIG. 4 is a plan view in the caudal direction of the apical vertebra of the scoliotic spine in FIG. 1 in its scoliotic configuration (ghost lines) and its treated configuration after the TSRH instrumentation is rotated from its scoliotic configuration to its kyphotic configuration;

FIG. 5 is a perspective view from the concave and posterior side of the scoliotic spine of FIG. 1 with a tool formed in accordance with the present invention attached to the TSRH instrumentation;

FIG. 6 is a perspective view from the concave and posterior side of the scoliotic spine of FIG. 5 after the derotation rod has been rotated to place the TSRH instrumentation in its kyphotic configuration and the spine has been derotated in accordance with the present invention;

FIG. 7 is a plan view in the caudal direction of the apical vertebra of the scoliotic spine in FIG. 6 showing its scoliotic configuration (ghost lines) and its derotated configuration (solid lines);

FIG. 10 is a perspective view of a portion of the tool of FIG. 8 showing the hooks for attachment to a derotation rod and a force imparting rod; and FIG. 11 is a perspective view of a portion of a second embodiment of the tool formed in accordance with the present invention.

DETAILED DESCRIPTION OF THE PREFERRED EMBODIMENT

Figure 8:
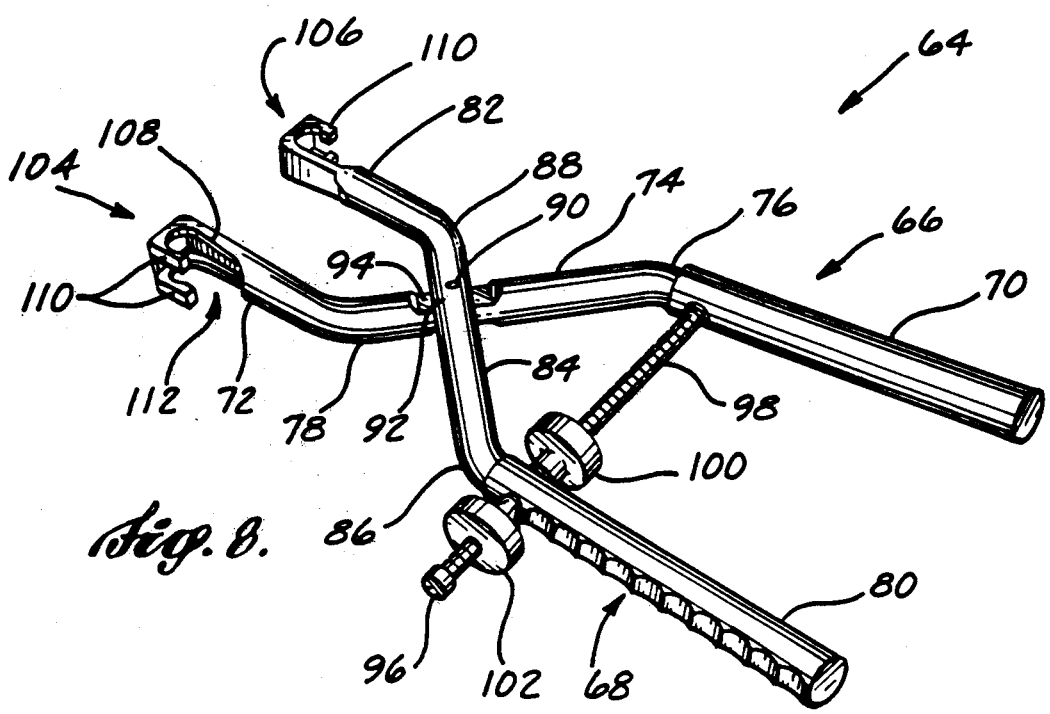
FIG. 8 is a perspective view of a tool used to derotate a scoliotic spine formed in accordance with the present invention.

In the following description of the method and tool for derotating a scoliotic spine formed in accordance with the present invention, the method and tool are described in conjunction with Cotrel-Dubousset instrumentation (hereinafter referred to as C-D instrumentation) which was developed between 1978 and 1983 and Texas Scottish Rite Hospital Universal Spinal Instrumentation which was developed beginning in 1985 (TSRH instrumentation). The C-D instrumentation and technique are described in detail in *Cotrel-Dubousset Instrumentation in the Treatment of Idiopathic Scoliosis* by Francis Denis, M.D., Orthopedic Clinics of North America-Vol. 19, No. 2, April 1988 and *Cotrel-Dubousset Instrumentation*, Richard A. Balderston, pages 113–126; *Spinal Instrumentation*, editors Howard S. An and Jerome M. Cotler, 1992. The TSRH instrumentation and technique are described in detail in the *Texas Scottish Rite Hospital Universal Spinal Instrumentation System* by Charles E. Johnston et al., pages 127–165; *Spinal Instrumentation*, editors Howard S. An and Jerome M. Cotler, 1992. The subject matter of these publications is expressly incorporated herein by reference.

Referring to FIG. 1, scoliotic spine 30 includes an abnormal lateral curvature 32. Lateral curvature 32 is centered around an apical vertebra 34 which lies at the apex of the curvature. Lateral curvature 32 has a convex side 36 and a concave side 38. Concave side 38 is the inside surface of lateral curvature 32 and convex side 36 is the outer surface of lateral curvature 32. In scoliotic spine 30, apical vertebra 34 and four or five vertebrae on each side of apical vertebra 34 are rotated into lateral curvature 32 such that the transverse processes 40 on concave side 36 are displaced in an anterior direction and transverse processes 42 on convex side 36 are displaced in the posterior direction.

TSRH instrumentation includes derotation rod 44 which has a scoliotic configuration and a kyphotic configuration. In FIG. 1, derotation rod 44 is in its scoliotic configuration and is secured to concave side 38 of scoliotic spine 30 around apical vertebra 34 using two basic types of hooks. The two basic types of hooks are a pedicle hook and a laminar hook. The hooks are designed to achieve secure anchoring on the pedicle, the lamina, and the transverse processes of various vertebrae. The number of hooks, the types, and their location will be determined by the practitioner depending on the particular patient's needs. Derotation rod 44 includes a superior end 46 which includes a squared head 48. Squared head 48 is engaged by wrench 50. Wrench 50 is relied upon to rotate derotation rod 44 in the direction of arrow 52 as described below in more detail.

The TSRH technique involves standard exposure of the scoliotic spine allowing exposure of the transverse processes of the upper end vertebrae and of the inferior aspect of the lamina of the lower end vertebrae. After exposure, placement of laminar and pedicle hooks is carried out according to conventional protocol. The publications referred to above provide guidance to the skilled artisan of operative planning for placement of the hooks, as well as a description of the actual instrumentation of the spine. After the hooks are inserted in the spine, a derotation rod is contoured and then inserted into the placed hooks. The derotation rod is contoured to have a scoliotic configuration which tends to match the lateral curvature of the scoliotic spine on its concave side. After the rod is inserted into the hooks in accordance with the TSRH technique, it is rotated such that the curvature of the rod is displaced approximately 90° in the posterior direction into the lateral curvature of the spine. Rotation of the derotation rod straightens the spine by pulling the concavity out of the lateral curvature.

Referring additionally to FIG. 2, in its normal configuration 54, shown in ghost lines, transverse processes 40 and 42 of apical vertebra 34 are in a neutral position.

When the scoliotic deformation occurs, transverse process 42 is displaced in the posterior direction while transverse process 40 is displaced in the anterior direction. This "rotation" of apical vertebra 34 is in the direction of arrow 56. The rotated scoliotic configuration 58 of apical vertebra 34 is shown in solid lines. When scoliotic spine 30 is treated in accordance with the TSRH technique, derotation rod 44 is rotated by wrench 50 in the direction of arrow 52 in FIG. 1 to shift the curvature of derotation rod 44 90° in the posterior direction. This position is shown in FIG. 3. Rotation of derotation rod 44 pulls lateral curvature 32 in the direction of concave side 38 and thus straightens the spine. Shifting the curvature in the derotation rod 90° in the posterior direction also pulls the concave side of the scoliotic spine in the posterior direction.

Referring additionally to FIG. 4, scoliotic configuration 58 of apical vertebra 34 prior to rotation of derotation rod 44 is shown in ghost lines with transverse process 42 displaced in the posterior direction and the transverse process 40 displaced in the anterior direction. After derotation rod 44 is rotated 90° in the posterior direction, lateral curvature 32 is reduced; however, referring to FIG. 4, the full line illustration of apical vertebra 34 shows treated configuration 60 and how apical vertebra 34 continues to have transverse process 42 displaced in the posterior direction and transverse process 40 displaced in the anterior direction. FIG. 4 also illustrates how concave side 38 is pulled in the direction of arrow 62 (i.e., posterior direction) and kyphosis is reintroduced into the spine. Unfortunately, the TSRH technique does little to reduce the rotation of apical vertebra 34.

Referring to FIGS. 5, 6 and 7, derotation of the spine is carried out in accordance with the present invention by exerting force in an anterior direction on convex side 36 of scoliotic spine 30 during rotation of derotation rod 44. This "derotation" force is provided without instrumentation of convex side 36 of scoliotic spine 30. Less instrumentation during treatment means less risk of damage to the spinal cord. The method carried out in accordance with the present invention achieves effective derotation of apical vertebra 34 and the vertebrae adjacent apical vertebra 34. The method uses a tool 64 which is secured to the derotation rod and includes a force imparting rod or means for attachment to a force imparting rod. The force imparting rod is used to apply an external force in an anterior direction on the convex side of the scoliotic spine during rotation of the derotation rod used in the TSRH technique. Before describing the method in more detail, tool 64 is described below.

Referring to FIG. 8, tool 64 formed in accordance with the present invention resembles a pair of pliers or a pair of scissors. As described above, tool 64 is designed to be secured to a derotation rod and a force imparting rod which is used to exert force on the convex side of a scoliotic spine during rotation of the derotation rod. Tool 64 includes two elongate arm members 66 and 68. First elongate arm member 66 includes a handle 70, nose 72, and neck 74. Handle 70 is connected to neck 74 by an elbow 76. Elbow 76 forms an obtuse angle between handle 70 and neck 74. The opposite end of neck 74 is attached to nose 72 by another elbow 78. Elbow 78 forms an obtuse angle between nose 72 and neck 74. Second elongate arm member 68 is substantially a mirror image of first elongate arm member 66. Second elongate arm member 68 includes handle 80, nose 82, neck 84, elbow 86, and elbow 88 that are substantially identical to handle 70, nose 72, neck 74, elbow 76, and elbow 78 of first elongate arm member 66.

Neck 74 and neck 84 are pivotally connected to each other at their pivot point 90. Accordingly, first elongate arm member 66 is pivoted to second elongate arm member 68 in much the same way the arms of a pair of pliers are connected. As with a pair of pliers, when the handles 70 and 80 are brought closer together, the distance between noses 72 and 82 increases. Conversely, when the distance between handles 70 and 80 increases, the distance between noses 72 and 82 decreases. Handles 70 and 80, necks 74 and 84, and noses 72 and 82 are generally tubular in the embodiment illustrated in FIG. 8. Pivot point 90 illustrated in FIG. 8 between elongate arm members 66 and 68 is a tongue and groove configuration. Elongate arm member 68 includes a channel 92 machined through its center. Elongate arm member 66 includes a narrowed tongue portion 94 which is received within channel 92 and is rotatably fixed therein by a pivot pin which passes through each arm member in a direction perpendicular to channel 92. While this is one embodiment of pivot connection 90, it should be understood that other types of pivot connections will be suitable.

In the illustrated embodiment, handles 70 and 80 are textured for ease of gripping.

Secured to handle 70 adjacent elbow 76 is an adjustment bolt 96. Adjustment bolt 96 is perpendicular to handle 70 and also passes through handle 80 adjacent elbow 86. Adjustment bolt 96 includes threads 98 and carries an inner adjustment nut 100 and an outer adjustment nut 102. Inner adjustment nut 100 and outer adjustment nut 102 are positioned on opposite sides of handle 80. The spacing between handle 80 and handle 70 can be adjusted by the positions of inner adjustment nut 100 and outer adjustment nut 102. Furthermore, inner adjustment nut 100 and outer adjustment nut 102 can be used to anchor to fix the relative position of handles 70 and 80. Naturally, this also fixes the distance between nose 72 and nose 82.

Figure 9:
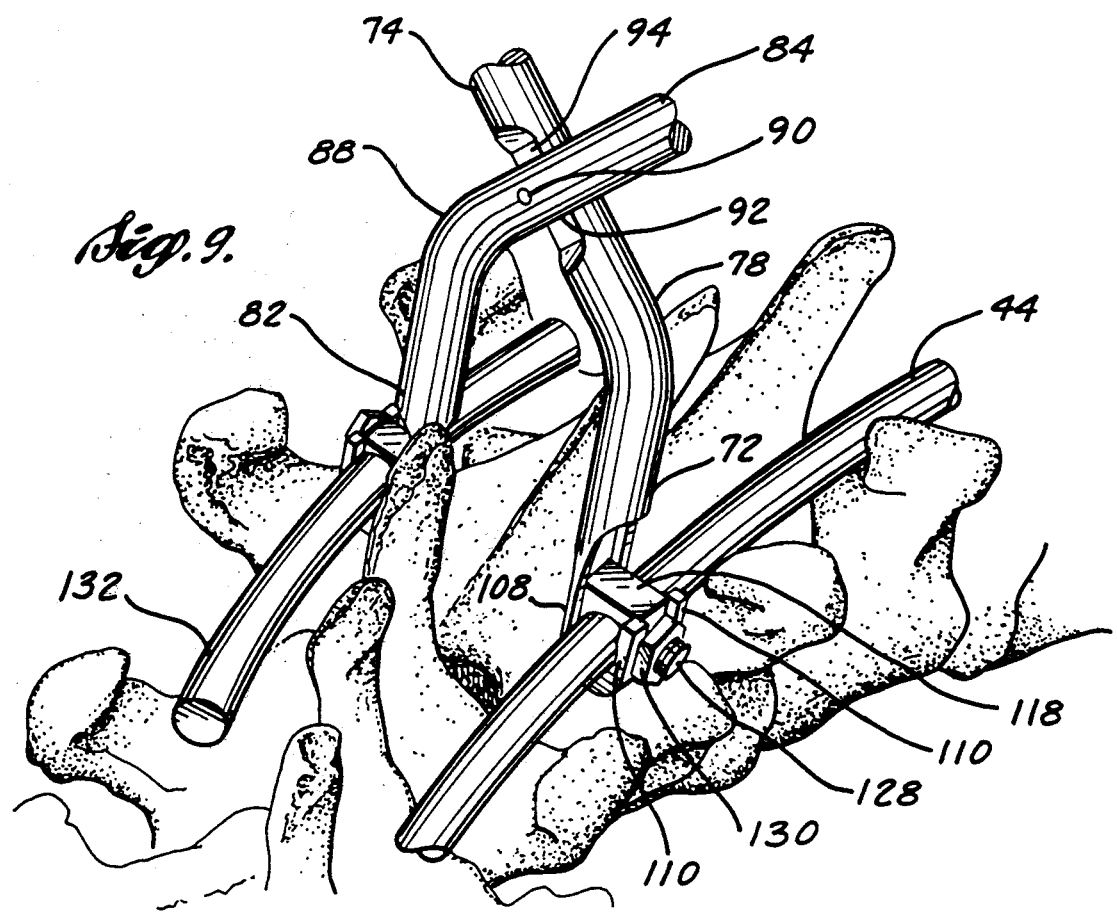
FIG. 9 is a perspective view of a portion of the tool formed in accordance with the present invention attached to a derotation rod and positioned adjacent a scoliotic spine.

Referring additionally to FIGS. 9 and 10, in the illustrated embodiment, nose 72 and nose 82 are each provided with coupling members 104 and 106, respectively. Coupling member 104 includes a shaft 108 and two spaced-apart tips 110. Coupling member 104 includes a channel 112 that separates shaft 108 from tips 110. Channel 112 is dimensioned to rotatably receive derotation rod 44. Tips 110 are spaced apart sufficiently to enable eyebolt 116 to pass between them. Eyebolt 116 includes a cube shaped body 118 with a bore 120 extending through opposing faces 122 and 124 of body 118. Bore 120 is sized to rotatably receive derotation rod 44. Extending from a surface 126 of eyebolt 116 that joins faces 122 and 124 is a threaded bolt 128. Bolt 128 receives nut 130 which is sized so that it cannot pass between tips 110. When eyebolt 116 is positioned between tips 110 and shaft 108, bore 120 lines up with channel 112 and bolt 128 extends between tips 110. Nut 130 threads onto bolt 128 and draws body 118 against the inside surface of tips 110 to eyebolt 116 in coupling member 104. Body 118 and bolt 128 are sized so that eyebolt 116 is secured in coupling member 104, yet derotation rod 44 is free to rotate.

In the embodiment illustrated in FIGS. 9 and 10, nose 82 includes coupling member 106 which is identical to coupling member 104 for securing force imparting rod 132. Force imparting rod 132 has a diameter substantially identical to derotation rod 44, however, it is generally shorter than derotation rod 44.

Referring to FIG. 11, in an alternative embodiment, tool 134 is identical to tool 64, except nose 136 that is opposite nose 138 includes an inverted coupling member 140 that is opened downward so that it will receive force imparting rod 132 from below. Tool 134, which includes inverted coupling member 140 is able to exert force on the force imparting rod 132 in an anterior direction without requiring that force imparting rod 132 be independently secured to coupling member 140.

Referring to FIGS. 5, 6, 7 and 9, tool 64 described above can be used in accordance with the method carried out in accordance with the present invention, as described below. First, scoliotic spine 30 must be provided with the TSRH instrumentation in accordance with conventional techniques. Thereafter, tool 64 is attached to derotation rod 44 using coupling member 104 in combination with eyebolt 116 described above with reference to FIG. 10. After tool 64 is rotatably secured to derotation rod 44, force imparting rod 132 is secured to coupling member 106. Alternatively, force imparting rod 132 can be secured to coupling member 106 before tool 64 is secured to derotation rod 44. Force imparting rod 132 has a curvature to match lateral curvature 32 of scoliotic spine 30 on convex side 36. Spacing between coupling members 104 and 106 should be adjusted using adjustment bolt 96, inner adjustment nut 100, and outer adjustment nut 102 so that force imparting rod 132 rests on transverse processes 42. After tool 64 is secured to derotation rod 44, derotation rod 44 is rotated by wrench 50 in the direction of arrow 144. Tool 64 is manually biased in the direction of arrow 146 to exert force in the anterior direction on convex side 36 of scoliotic spine 30. This force pushes transverse processes 42 in the anterior direction and derotates the scoliotic spine.

Referring specifically to FIG. 7, the ghost line depiction of apical vertebra 34 shows the scoliotic position 158 identical to the ghost line depiction in FIG. 4. Solid line 160 depiction in FIG. 7 shows the treated position 160 of apical vertebra 34 after treatment by the method and tool of the present invention. Arrow 148 indicates the direction of the displacement and derotation of apical vertebra 34. The relative position of derotation rod 44 and tool 64 after derotation of scoliotic spine 30 is shown in FIG. 6. FIG. 7 illustrates how the method and tool formed in accordance with the present invention are able to "derotate" apical vertebra 34 and the vertebrae adjacent thereto in conjunction with reducing lateral curvature of the spine.

The method and tool formed in accordance with the present invention allow active force to be applied to the convex side of a scoliotic spine in an anterior direction which allows the practitioner to effectively derotate the spine at the same time that the lateral curvature of the scoliotic spine is being treated. The method and tool formed in accordance with the present invention allow the practitioner to achieve derotation that in the past have not been achievable. The method and tool are uniquely compatible with existing techniques and should be capable of use by practitioners with reasonable amounts of training.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A tool for applying force in an anterior direction on a convex side of a scoliotic spine during rotation of a derotation rod attached to a concave side of the scoliotic spine, the application of the force reducing rotational deformity of the scoliotic spine, the tool comprising:

first arm member including a first handle end and a first nose end opposite the first handle end, the first handle end and the first nose end connected by a first neck;

second arm member including a second handle end and a second nose end opposite the second handle end, the second handle end and second nose end connected by a second neck;

pivotal connection securing the first neck to the second neck;

first coupling member secured to the first nose end including a channel open towards the first handle member for securing the first arm member to the derotation rod; and second coupling member secured to the second nose end for securing the second arm member to a force imparting rod.

2. The tool of claim 1, further comprising an adjustment bolt secured to the first arm member and slidably engaging the second arm member, the adjustment bolt carrying an inner adjustment nut and an outer adjustment nut, the inner and outer adjustment nuts being on opposite sides of the second arm member.

3. The tool of claim 1, wherein the first arm member and the second arm member are pivoted to each other in a scissor-like manner.

4. The tool of claim 3, wherein the pivotal connection is a tongue and groove arrangement.

5. The tool of claim 5, wherein the channel is defined between the first nose end and two spaced-apart fingers, the first nose end defining one side of the channel and the spaced-apart fingers defining an opposite side of the channel.

6. A tool for applying force in an anterior direction on a convex side of a scoliotic spine during rotation of a derotation rod attached to a concave side of the scoliotic spine, the application of the force reducing rotational deformity of the scoliotic spine, the tool comprising:

first arm member including a first handle end and a first nose end opposite the first handle end, the first handle end and the first nose end connected by a first neck;

second arm member including a second handle end and a second nose end opposite the second handle end, the second handle end and second nose end connected by a second neck;

pivotal connection securing the first neck to the second neck;

first coupling member secured to the first nose end including a channel open towards the first handle member for securing the first arm member to the derotation rod; and a force imparting rod secured to the second nose end having a longitudinal axis that is parallel to the channel.

7. The tool of claim 6, further comprising an adjustment bolt secured to the first arm member and slidably engaging the second arm member, the adjustment bolt carrying an inner adjustment nut and an outer adjustment nut, the inner and outer adjustment nuts being on opposite sides of the second arm member.

8. The tool of claim 6, wherein the first arm member and the second arm member are pivoted to each other in a scissor-like manner.

9. The tool of claim 8, wherein the pivotal connection is a tongue and groove arrangement.

10. The tool of claim 6, wherein the channel is defined between the first nose end and two spaced-apart fingers, the first nose end defining one side of the channel and the spaced-apart fingers defining an opposite side of the channel.

11. A tool for applying force in an anterior direction on a convex side of a scoliotic spine during rotation of a derotation rod attached to a concave side of the scoliotic spine, the application of the force reducing rotational deformity of the scoliotic spine, the tool comprising:

first arm member including a first handle end and a first nose end opposite the first handle end, the first handle end and the first nose end connected by a first neck;

second arm member including a second handle end and a second nose end opposite the second handle end, the second handle end and the second nose end connected by a second neck;

pivotal connection securing the first neck to the second neck;

first coupling member secured to the first nose end for securing the first arm member to the derotation rod; and a force imparting rod shaped to the contour of the convex side of the scoliotic spine secured to the second nose end.

12. A method for reducing rotational deformity of a scoliotic spine having a convex side and a concave side, the method comprising the steps:

connecting a derotation rod to the scoliotic spine using multiple hooks, the derotation rod having a scoliotic configuration and a kyphotic configuration;

rotating the derotation rod from its scoliotic configuration to its kyphotic configuration using a tool comprising a first arm member including a first handle end and a nose end opposite the first handle end, the first handle end and the first nose end connected by a first neck, a second arm member including a second handle end and a second nose end opposite the second handle end, the second handle end and second nose end connected by a second neck, a pivotal connection securing the first neck to the second neck, a first coupling member secured to the first nose end including a channel open towards the first handle member for securing the first arm member to the derotation rod and a second coupling member secured to the second nose end for securing the second arm member to a force imparting rod; and reducing the rotational deformity of the scoliotic spine by applying force to the convex side of the scoliotic spine in an anterior direction during the rotating step.

13. The method of claim 12, further comprising, after the connecting step, securing the tool to the derotation rod for applying a force to the convex side of the scoliotic spine in an anterior direction during the rotating step.

14. The method of claim 13, wherein the reducing step further comprises displacing the convex side of the scoliotic spine in an anterior direction during the rotating step.

15. The method of claim 14, wherein during the rotating step the tool is manually biased in a direction opposite the direction the derotation rod is rotated.

16. A method for reducing rotational deformity of a scoliotic spine having a convex side and a concave side, the method comprising the steps:

connecting a derotation rod to the scoliotic spine using multiple hooks, the derotation rod having a scoliotic configuration and a kyphotic configuration;

rotating the derotation rod from its scoliotic configuration to its kyphotic configuration using a tool that includes a first arm member including a first handle end and a first nose end opposite the first handle end, the first handle end and the first nose end connected by a first neck, a second arm member including a second handle end and a second nose end opposite the second handle end, the second handle end and second nose end connected by a second neck, a pivotal connection securing the first neck to the second neck, first coupling member secured to the first nose end including a channel open towards the first handle member for securing the first arm member to the derotation rod, and a force imparting rod secured to the second nose end having a longitudinal axis that is parallel to the channel; and reducing the rotational deformity of the scoliotic spine by applying force to the convex side of the scoliotic spine in an anterior direction during the rotating step.

17. The method of claim 16, further comprising, after the connecting step, securing the tool to the derotation rod for applying a force to the convex side of the scoliotic spine in an anterior direction during the rotating step.

18. The method of claim 17, wherein the reducing step further comprises displacing the convex side of the scoliotic spine in an anterior direction during the rotating step.

19. The method of claim 18, wherein during the rotating step the tool is manually biased in a direction opposite the direction the derotation rod is rotated,.

* * * * *

UNITED STATES PATENT AND TRADEMARK OFFICE
CERTIFICATE OF CORRECTION

PATENT NO. : 5,281,223
DATED : January 25, 1994
INVENTOR(S) : R. Charles Ray

It is certified that error appears in the above-indentified patent and that said Letters Patent is hereby corrected as shown below:

| COLUMN | LINE | |
|---|---|---|
| [56] "Foreign Patents" | 4th Ref. | Please add --22578  1893  British-- |
| [56] "Other Publications" | 5th Publn. | "pp. 16-254" should read --pp.16-25-- |
| 6 | 38 | "to" (second occurrence) should read --or-- |
| 8 (Claim 5 Line 1) | 38 | "claim 5" should read --Claim 1-- |
| 10 (Claim 19 Line 3) | 58 | "rotated,." should read --rotated.-- |

Signed and Sealed this

Eleventh Day of April, 1995

Attest:

BRUCE LEHMAN

*Attesting Officer*   *Commissioner of Patents and Trademarks*